United States Patent [19]

Chang

[11] Patent Number: 4,829,010
[45] Date of Patent: May 9, 1989

[54] IMMUNOASSAY DEVICE ENCLOSING MATRIXES OF ANTIBODY SPOTS FOR CELL DETERMINATIONS

[75] Inventor: Tse W. Chang, Houston, Tex.

[73] Assignee: Tanox Biosystems, Inc., Houston, Tex.

[21] Appl. No.: 25,501

[22] Filed: Mar. 13, 1987

[51] Int. Cl.$^4$ ................... G01N 33/543; G01N 1/48; C12M 1/22

[52] U.S. Cl. ................................. 422/58; 436/532; 436/807; 436/809; 435/298; 422/58

[58] Field of Search .............. 436/527, 532, 807, 809, 436/518; 435/297-298; 422/57, 58

[56] References Cited

U.S. PATENT DOCUMENTS

| | | | |
|---|---|---|---|
| 3,165,450 | 3/1963 | Scheidt | 435/298 |
| 4,055,394 | 10/1977 | Friedman et al. | 23/253 |
| 4,154,795 | 5/1979 | Thorne | 422/99 |
| 4,216,245 | 8/1980 | Johnson | 427/2 |
| 4,228,127 | 10/1980 | Acevedo et al. | 422/61 |
| 4,315,907 | 10/1982 | Fridlender et al. | 422/61 |
| 4,317,810 | 3/1982 | Halbert et al. | 424/12 |
| 4,357,142 | 11/1982 | Shall, Jr. et al. | 23/230 B |
| 4,468,371 | 8/1984 | Chen et al. | 422/102 |
| 4,471,056 | 9/1984 | Grumet et al. | 436/513 |
| 4,591,570 | 2/1983 | Chang | 436/519 |
| 4,647,430 | 3/1987 | Zweig | 422/58 |
| 4,708,933 | 6/1984 | Huang et al. | 436/527 |
| 4,761,381 | 8/1988 | Blatt et al. | 422/57 |

FOREIGN PATENT DOCUMENTS 0063810 11/1982 European Pat. Off. .
0200507 11/1986 European Pat. Off. .
59-94068 5/1984 Japan .
84/03151 8/1984 PCT Int'l Appl. .

OTHER PUBLICATIONS

Tse Wen Chang, "Binding of Cells to Matrixes of Distinct Antibodies Coated on Solid Surface", 1983, pp. 217-223.

Paul Herbrink, Frans J. Van Bussel & Sven O. Warnaar, "The Antigen Spot Test (AST): A Highly Sensitive Assay for the Detection of Antibodies", 1981, pp. 293-298.

Langone et al., EDS1, "Immunochemical Techniques", Part C., pp. 90-105, by Sedlacek, H. H., et al., 1981.

Eva Engvall & Peter Perlmann, "Enzyme-Linked Immunosorbent Assay, Elisa", 1971, pp. 129-135.

Richard Hawkes, Evelyn Niday, & Julian Gordon, "A Dot-Immunobinding Assay for Monoclonal & Other Antibodies", 1981, pp. 142-147.

Michaelsen et al., Chemical Abstracts: 97:37269Y (1982). Abstract of "Sheep, Rabbit and Chicken Antisera Against a Human $V_H$ Fragment: Reactivity with Immunoglobins and Lumphocytes".

Primary Examiner—Sidney Marantz
Assistant Examiner—Lyle Alfandary-Alexander
Attorney, Agent, or Firm—Hamilton, Brook, Smith & Reynolds

[57] ABSTRACT

An immunoassay device comprising a support which has a substantially planar surface 14 on which is located an array of small, closely-spaced, discrete, antibody coated areas (spots) 17. A cover 16 is spaced from the support surface 14 and is positioned over the array of antibody coated spots 17. The cover is attached to the support surface to provide an enclosed chamber 30. In the cover there is at least one aperture communicating with the interior of the chamber 30 for introducing a liquid sample into the chamber. In addition, there is at least one additional aperture 34 in the cover, which also communicates with the interior of the chamber to allow air to escape upon introduction of the sample into the chamber. When a cell sample is introduced into the chamber it immediately fills the chamber and cells will settle uniformly over the matrix. The antibody-coated spots function as tiny immunoadsorbents for cells bearing antigens recognized by the antibody. The device can be used to determine the proportion of cells in a sample cell population.

36 Claims, 1 Drawing Sheet

IMMUNOASSAY DEVICE ENCLOSING MATRIXES OF ANTIBODY SPOTS FOR CELL DETERMINATIONS

BACKGROUND

The detection of a cell surface antigen by its specific reactivity with an antibody can be performed in several ways. Immunofluorescence staining, radiobinding assays, agglutination assays and complement-mediated cell lysis are the most commonly used methods. In all these procedures, the determination of the reactivity of the cells with each antibody is handled separately, i.e. the cells are incubated separately in a tube or in a well of a microwell plate, etc. with each antibody to be tested.

In U.S. Pat. No. 4,591,570, an immunoassay device, called an "antibody matrix" device, is disclosed which allows simultaneous determination of specific cell surface antigens in one reaction incubation by employing orderly arranged antibody spots on a solid surface. It was demonstrated that when an antibody-coated surface is used for the adsorbence of cells, reactive cells adhere microscopically uniformly over minute areas in different parts of the solid surface. Because of this property, antibodies of distinct specificities are coated on small, discrete areas in close proximity forming a matrix-like array on the surface. The spots act as tiny specific immunoadsorbents for cells bearing on their surface the antigens with which the antibodies react.

"Antibody matrix" devices can be used not only to determine the presence of a specific allotype of a surface antigen on the cells of an individual (such as tissue typing), but also to analyze functionally different cell subpopulations that express distinct differentiation antigens. The antibody-coated surfaces can adsorb quantitatively from a mixed population the cells that bear the specific cell surface antigen the antibody react with. Thus, the device can be used to determine the proportion of specific subsets in a mixed population of cells.

The "antibody matrix" device represents a major simplification of existing immunocytological and immunochemical methodology in that it eliminates the need for repetitive pipetting when a large number of tests for different antigens are performed. Other advantages are that all tests with antibodies may be performed simultaneously in one location, only a single application of sample is required as opposed to the repetitive pipetting of sample into a large number of separate wells or tubes, and very small amounts of sample and reagents are consumed.

SUMMARY OF THE INVENTION

An immunoassay device made in accordance with the principles of this invention comprises a support which has a substantially planar surface. On the support is an array of small, closely-spaced, discrete, antibody coated areas. A cover is spaced from the support surface and is positioned over the array of antibody coated areas. The cover is secured to the support surface to provide an enclosed chamber. In the cover there is at least one aperture communicating with the interior of the chamber for introducing a liquid sample into the chamber. In addition, there is at least one additional aperture in the cover, which also communicates with the interior of the chamber to allow air to escape upon introduction of the sample into the chamber.

A preferred way of securing the cover to the planar surface is by four walls which extend upwardly from the support surface and which are secured to the surface. They are arranged in the form of a rectangle which creates an enclosure located at the perimeter of the array of the antibody coated areas.

Preferably, the support and the cover are light transparent. The support surface may be glass or plastic microscope slides and the walls, as well as the cover, may be made of like material.

The cover may be flat and planar and supported by walls or may be arcuate in cross section being of unitary construction with its periphery secured directly to the support surface. The walls may be secured to the support surface by a plurality of downwardly depending dowels which fit within mating bores in the support surface or conversely, the dowels may be formed on the support surface and project into bores in the walls.

One or more separately enclosed arrays of antibody spots may be located on a single slide.

The enclosure may be compound, leaving two or more contiguous chambers of different volumes.

Depending upon the materials from which the device is made, the walls may be secured to the surface by appropriate adhesive material, and likewise, the cover may be secured to the top of the walls by appropriate adhesive material. The cover may be either permanently or detachably secured to the surface. For example a permanent or pressure sensitive adhesive may be used.

The antibody-coated areas (generally small dots of about 0.25 mm–2.0 mm in diameter) serve as antigen-specific immunoadsorbents. The areas specifically adsorb cells which express surface antigen recognized by the coated antibody. Thus, a cell can be identified as having a particular surface antigen by whether it adheres to a spot coated with a cognate antibody. In the preferred embodiment the density and distribution of antibody in the coated spots is such that when cells bearing a surface antigen are brought into contact in sufficient concentration with a discrete antibody-coated area containing antibodies which bind the antigen, the cells adhere tightly to the discrete, antibody coated area and distributed substantially microscopically uniformly are over the discrete antibody-coated area.

When a sample, e.g. a suspension of cells, is introduced into the sample chamber it will be evenly and uniformly distributed over all of the antibody coated areas (the test surface). The chamber has a defined height and thus, when a cell suspension is introduced in the chamber and the device is placed on a flat surface, each unit area of antibody-coated surface will receive the same number of cells. The number of cells on per unit area of antibody coated surface can be converted to the number of cells in each volume of original sample (such as blood).

The above and other features of the invention including various novel details of construction in combinations of parts, will now be more particularly described with reference to the accompanying drawings and pointed out in the Claims. It will be understood that the particular immunoassay device embodying the invention, is shown by way of illustration only, and not as a limitation of the invention. The principles and features of this invention may be employed in varied and numerous embodiments without departing from the scope of the invention.

DETAILED DESCRIPTION OF THE INVENTION

Figure 1:
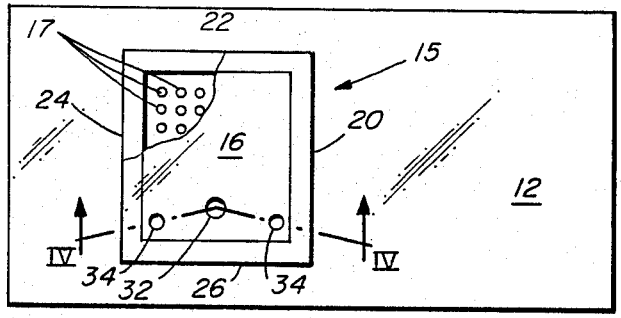
FIG. 1 is a plan view of an immunoassay device embodying the features of the present invention.
Figure 2:
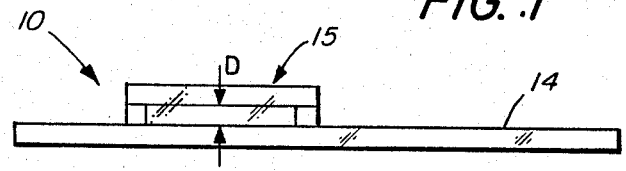
FIG. 2 is a side view thereof.
Figure 3:
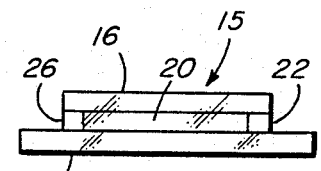
FIG. 3 is an end view thereof.
Figure 4:
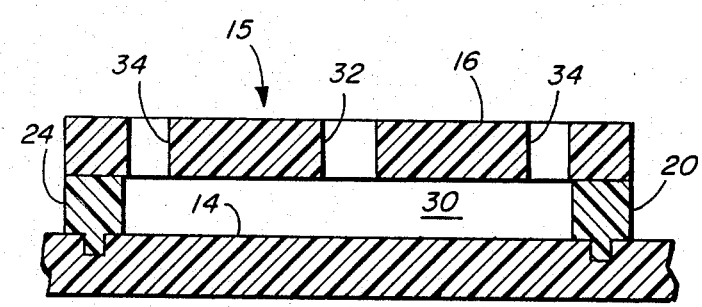
FIG. 4 is a sectional view of a portion of the device on an enlarged scale taken along the lines IV—IV on FIG. 1.

An immunoassay device shown in the drawings is generally designated 10. It includes a support 12, having a substantially planar surface 14. An array of small, closely-spaced discrete antibody coated areas 16 are located in an enclosed chamber 15 on the support surface and are shown only partially in FIG. 1. The enclosed chamber 15 comprises a cover 16 is spaced from the support surface by a distance D, as shown in FIG. 2, and is located over the array of antibody coated areas 17.

As shown in FIGS. 1 through 4, the cover is supported on four walls 20, 22, 24 and 26 which are secured to the surface 14 of the support surface 12, and project upwardly therefrom. As herein disclosed they form a rectangular enclosure located at the perimeter of the array of antibody coated areas 16, but it should be understood that other configurations may be employed without departing from the scope or spirit of the invention.

The cover 16, being mounted on the walls, extends a distance D above the surface 14 of the support 12 to create, together with the walls a chamber 30. The smaller the dimension D the quicker the cells will settle on the antibody matrix. For example, 0.3 to 2 mm have been found satisfactory.

The cover includes at least one aperture 32, which communicates with the chamber 30 for the introduction of the sample into the chamber and there is at least one other aperture 34 (there being two shown in FIGS. 1 and 4) to permit the escape of air when a sample is introduced into the chamber.

Figure 8:

As will be seen in FIG. 8, the cover and the walls may be integral, again creating a chamber 30 defined by the surface 14 of the support and the interior of a unitary member 36.

Figure 9:
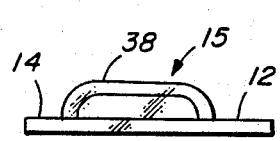
FIGS. 9 through 11 show other embodiments of the invention on a reduced scale.

The cover and walls may also be unitary being formed as a bubble or arcuate dome 38 as seen in FIG. 9.

Figure 10:
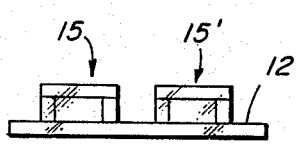

As seen in FIG. 10, there may be two or more enclosed chambers, 15 and 15' on one support, each one enclosing a matrix of antibody spots. This will allow samples of two different cell concentrations to be tested.

Figure 11:
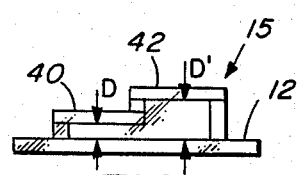

As seen in FIG. 11, the enclosed chamber 15 may also have two (or more) steps 40 and 42 of defined heights (distances D and D'). Thus, a single sample introduced into the chamber provides a different number of cells to matrices of antibody coated areas located under each step.

Figure 5:
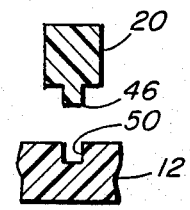
FIG. 5 is a detailed sectional view of one form of means for securing the walls to the support surface.
Figure 6:
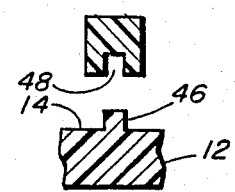
FIG. 6 is an alternative means of supporting and locatig the walls.
Figure 7:
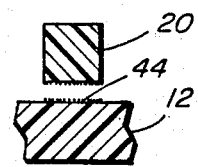
FIG. 7 is yet another alternative embodiment for the means for supporting the walls.

FIGS. 5 through 7 show various means of securing the walls to the support. FIG. 7 shows the wall 20 secured to the support 12 by adhesive material 44 either permanent or pressure sensitive which is compatible with the materials from which the immunoassay device is made.

FIG. 6 shows a dowel 46 projecting upwardly from the surface 14 of the support 12 which is engaged within a mating cylindrical opening 48 in the wall 20.

Conversely, the dowel 46 may be formed on the wall 20 and projected downwardly into a cylindrical opening 50 in the surface 14 of the support 12.

The function of the array of antibody coated areas as a test surface is described in detail in U.S. Pat. No. 4,591,570, the teachings of which are incorporated herein by reference. The antibody-coated areas form small spots on the surface of the support surrounded by uncoated surface space. The antibodies in the antibody coated spots are conjugated to the surface of the support; they may be either covalently or non-covalently bound thereto.

The preferred arrangement of the spots on the surface of the support is a rectangular (preferably square) matrix. A compact 5-20 matrix is preferred. A matrical arrangement permits any spot to be readily identified by reference to coordinates giving the row and column number of the particular spot. The antibody spots should be closely spaced, thereby minimizing the surface space occupied by the complete arrangement of spots and in turn, maximizing the uniformity of cell suspension with which the antibody dots come into contact, and minimizing the amount of sample needed. For instance, a 10 spot by 10 spot matrix should occupy about 1 $cm^2$ or less of the surface of the support.

The support surface 14, in the region or field of the antibody matrix, can be coated with an inert visible material except where the antibody-coated spots 17 are located. This outlines the antibody spot array. The material can be water repellant. A preferred material is tetrafluoroethylene or fluorinated ethylene-propylene. The inner surface of the walls may also be coated with a water repellant material.

In accordance with the invention, each spot, or each of certain sets of spots (such as the spots in one row or column), is made up of antibodies of single distinct specificity. Each spot 16, (or each set of spots), contains antibodies whose specificity is different from the specificity of antibodies in the other spots. Thus, in an 100 spot matrix, 100 antibodies of different specificty may be tested, or, if only 10 different antibodies are tested, each of them can be repeated 10 times. The antibody-coated spots serve as minute, specific immunoadsorbents for antigens with which the antibodies react. Antibody-coated spots made up of antibodies directed against a particular surface antigen of cells serve as specific immunoadsorbents for cells bearing that surface antigen. Cell adherence to a spot indicates the presence of the antigen on the cell.

The density of antibodies in the antibody-coated spots is related to the function of the spots as immunoadsorbents of cells. The density of coated antibodies, (either covalently or non-covalently conjugated to the surface of the support), must be such that the cells bind tightly to the spots and remain bound during ordinary manipulation of the device in subsequent procedures for detecting cell binds. It is suspected that bridges between the surface antigens of the cells and the antibodies attached to the surface of the support must be sufficiently numerous in order to achieve tight cell binding. Preferably, however, the density of antibodies should be sufficient to yield, upon contact with an appropriate concentration of cells which have surface antigens that bind to the antibodies, a microscopically uniform layer of bound cells covering the entire antibody-coated spot. The formation of such a uniform distribution of cells is desirable because it facilities detection of spots to which cells have attached. The density required to generate a microscopically uniform distribution of cells is probably greater than the density minimally sufficient for tight cell binding.

The immunoassay device of this invention can be produced by applying small volumes of antibody solutions to the support surface 14 and allowing the solutions to remain on the support 14 until the antibodies become adsorbed to the surface. If desired, the antibodies may be chemically bound to the surface of the support by employing conventional methods for covalently binding proteins to a solid phase.

Preferred antibodies for use in the device are monoclonal antibodies. Because the binding of protein to the support surface is dependent on its proportion in solution as well as its concentration, solutions of antibodies must be highly purified in order to obtain a sufficiently dense antibody coat for cell adherance. Monoclonal antibodies can be obtained in sufficiently pure solutions for preparing the antibody-coated spots. However, antigenspecific polyclonal antibodies can also be purified for the purpose of this invention.

Antibody spots 16 of sufficient density for cell adherence can be obtained by applying solutions of antibody to the support surface having from about 10 $\mu$g/ml to about 20 $\mu$g/ml protein and being at least about 50% preferably greater than about about 80% pure.

The device can be used for antigen determinations as follows. A sample of cells to be tested is placed in suspension in a suitable medium (for example, normal saline). The sample is introduced into the sample chamber 30. The volume of cell suspension needed to fill the chamber 30 and to cover the entire antibody matrix depends upon the size of the chamber. For example, for a 1.2 cm $\times$ 1.2 cm (inner dimension) size chamber of 1 mm height, about 150 $\mu$l of cell suspension is required to fill the chamber.

After the cells are introduced into the chamber 30, they are allowed to settle on the test surface, which takes about 5 minutes for a chamber of 1 mm height. After an appropriate reaction time, which is about 20 minutes for a typical procedure. Non-adherent cells are removed from the test surface. This can be accomplished by flushing the chamber 30 with a wash solution. If the chamber cover 16 is detachable it may be removed and the test surface washed. The device may be agitated during the washing step.

The matrix of antibody spots is then examined to determine the numbers or amounts of cells bound to each individual spot. The binding of some or all cells to a particular spot indicates that the cells express antigen recognized by the antibody in the spot. Cells may be fixed and stained to aid in quantitation of cells. The number of cells adhered to a spot will indicate the relative proportions of antigen-bearing cells in the original cell suspension.

The chamber construction of the immunoassay device provides a number of advantages. When a cell solution is introduced into the chamber it will immediately spread out into the entire chamber space. Antibody spots will be distributed with equal number of cells so that comparison of cell adhesion between spots is accurate. The defined height of the chamber also enables the determination of the numbers of cells per unit volume of cell suspension based upon the numbers of cells per unit area of a spot.

The chamber also facilitates the handling of samples. It reduces spillage and dispenses with the need to premeasure sample volume.

Equivalents

Those skilled in the art will recognize, or be able to ascertain using no more than routine experimentation, many equivalents to the specific embodiments of the invention described herein. Such equivalents are intended to be encompassed by the following claims.

I claim:

1. An immunoassay device comprising:
   a. a support having substantially planar, unrestricted surface,
   b. an array of small, closely-spaced, discrete, antibody-coated areas on the support surface;
   c. a cover spaced from the support surface and positioned over an array of antibody-coated areas;
   the cover being secured to the support surface to provide a single, unrestricted, enclosed chamber,
   the cover having at least one aperture communicating with the interior of the single chamber and with ambient atmosphere for introducing a liquid sample into the chamber to flow across the planar surface without impediment and into engagement with all of said coated areas regardless of the location of the aperture relative to the planar surface, and
   at least one additional aperture in the cover also communicating with the interior of the chamber and ambient atmosphere to allow air to escape from the chamber upon introduction of the sample into the chamber.

2. An immunoassay device of claim 1, wherein all of the discrete, antibody-coated areas are of substantially the same size and shape.

3. An immunoassay device of claim 1 wherein the antibodies in the discrete antibody-coated surface areas are covalently bound to the surface of the support.

4. An immunoassay device according to claim 1, wherein the antibody in each of the discrete, antibody-coated surface areas, or in identifiable sets of said antibody-corated surface areas, is antibody of different and distinct specificity.

5. An immunoassay device according to claim 1, wherein the antibodies in the discrete, antibody-coated areas are highly purified polyclonal antibodies.

6. An immunoassay device according to claim 1, wherein the antibodies in the discrete, antibody-coated areas are monoclonal antibodies.

7. An immunoassay device according to claim 1, wherein the support is a glass microscope slide.

8. An immunoassay device according to claim 1, wherein the support is a plastic microscope slide.

9. An immunoassay device according to claim 1, wherein discrete, antibody-coated surface areas are dots having diameters of from about 0.25 mm to about 1.0 mm.

10. An immunoassay device according to claim 1, wherein said antibody-coated dots on the surface of the support are arranged in a compact 5-20 dot by 5-20 dot rectangular matrix.

11. An immunoassay device of claim 1, wherein the antibodies are adsorbed to the planar surface at a density and uniformity such that when cells bearing a surface antigen are brought into contact in sufficient concentration with a discrete antibody-coated area containing antibodies which bind the antigen, the cells adhere tightly to the discrete, antibody coated area and form a layer of bound cells which is substantially microscopically uniform over essentially all of the discrete antibody-coated area.

12. An immunoassay device of claim 1, wherein the antibody coated areas are formed by applying solutions of antibody to the support surface of from about 10 to about 20 μg/ml.

13. An immunoassay device of claim 1, wherein the cover is detachably secured to the surface of the support.

14. An immunoassay device of claim 1, wherein at least two arrays of antibody coated areas are located on the support.

15. An immunoassay device according to claim 1, wherein the array of discrete, antibody-coated areas is a rectangular matrix.

16. An immunoassay device according to claim 15, wherein the entire rectangular matrix is contained with an area of from about 0.5 to about 1.0 cm² of the surface of the support.

17. An immunoassay device of claim 1, wherein the cover is substantially rectangular and planar and is mounted upon walls which are secured to the surface of the support and extend upwardly therefrom.

18. An immunoassay device of claim 17, wherein the walls are secured to the planar support by projections extending between the wall and the planar surface.

19. An immunoassay device of claim 1, wherein the surface of the planar support is coated with a visible, inert, water repellant, material except where the antibody coated spots are located.

20. An immunoassay device of claim 19, wherein the coating material is tetrafluoroethylene or fluorinated ethylene-propylene.

21. An immunoassay device comprising:
 a. a support having a substantially planar, unrestricted surface,
 b. an array of small, discrete, closely-spaced, antibody-coated areas on the planar surface;
 c. walls extending upwardly from the support surface and secured to the surface to form a single rectangular enclosure located at the perimeter of the array of antibody-coated areas and defining the planar unrestricted surface within the walls, and
 d. a cover mounted on the walls thereby providing a single, unrestricted enclosed chamber,
 the cover having at least one aperture communicating with the interior of the chamber interior for introduction a sample into the chamber to flow across the planar surface without impediment and into engagement with all of said coated areas,
 and at least one other aperture also communicating with the chamber interior to permit the escape of air from the chamber when a sample is introduced into the chamber regardless of the location of either aperture relative to the planar surface.

22. An immunoassay device of claim 21, wherein all of the discrete, antibody-coated areas are of substantially the same size and shape.

23. An immunoassay device of claim 21, wherein the antibodies in the discrete antibody-coated surface areas are covalently bound to the surface of the support.

24. An immunoassay device according to claim 21, wherein the antibody in each of the discrete, antibody-coated surface areas, or in identifiable sets of said antibody-coated surface areas, is antibody of different and distinct specificty.

25. An immunoassay device according to claim 21, wherein the antibodies in the discrete, antibody-coated surface areas are highly purified polyclonal antibodies.

26. An immuncassay device according to claim 21, wherein the antibodies in the discrete, antibody-coated areas are monoclonal antibodies.

27. An immunoassay device according to claim 21, wherein the support is a glass or plastic microscope slides.

28. An immunoassay device according to claim 21, wherein the array of discrete, antibody-coated areas is a rectangular matrix.

29. An immunoassay device according to claim 21, wherein discrete, antibody-coated surface areas are dots having diameters of from about 0.25 mm to about 1.0 mm.

30. An immunoassay device of claim 21 wherein the antibodies are adsorbed to the planar surface at a density and uniformity such that when cells bearing a surface antigen are brought into contact in sufficient concentration wlth a discrete, antibody-coated area containing antibodies which bind the antigen, the cells adhere tightly to the discrete, antibody coated area and distribute substantially microscopically uniformly over essentially all of the discrete antibody-coated areas.

31. An immunoassay device of claim 21, wherein the antibody-coated areas are formed by applying solutions of antibody of from about 10 to about 20 μl/ml.

32. An immunoassay device of claim 21, wherein the surface of the planar support in the field of the antibody-coated areas is coated with a visible, inert layer except where the antibody coated spots are located.

33. An immunoassay device of claim 21, wherein the walls and cover are detachably secured to the support surface.

34. An immunoassay device according to claim 21, wherein said antibody-coated dots on the surface of the support are arranged in a compact 5-20 dot by 5-20 dot rectangular matrix.

35. An immunoassay device according to claim 34, wherin the entire rectangular matrix is contained within an area of from about 0.5 to about 1.0 cm² of the surface of the support.

36. An immunoassay device, comprising:
 a. a glass or plastic support having a substantially planar, unrestricted surface;
 b. two, separate rectangular arrays of antibody-coated dots on the planar surface, the density of antibody in the dots being about 10 μg/ml to 20 μg/ml;
 c. walls extending upwardly from the support surface and located at the perimeter of each array of antibody-coated dots and defining the planar, unrestricted surface within the walls; and
 d. a cover mounted upon the walls thereby forming an enclosed chamber over each array, the cover having a sample injection aperture communicating with the chamber space and a plurality of apertures also communicating with the chamber space to permit air to escape.

* * * * *